United States Patent [19]

Bowell

[11] 4,083,966

[45] Apr. 11, 1978

[54] METHOD OF EMULSIFYING MINERAL OIL

[76] Inventor: Harold James Perry Bowell, 7660 Canada Way, Burnaby, British Columbia, Canada, V3N 3K8

[21] Appl. No.: 636,352

[22] Filed: Nov. 28, 1975

[51] Int. Cl.$^2$ .......................... A01N 9/04; A61K 7/42
[52] U.S. Cl. ............................ 424/170; 424/DIG. 10; 424/59
[58] Field of Search .................. 424/DIG. 10, 59, 170

[56] References Cited

U.S. PATENT DOCUMENTS 1,927,916   9/1933   Brown et al. .................... 424/168 X

OTHER PUBLICATIONS

Martindale Extra Pharmacopoeia, 1958, pp. 1290-1293.
Technical Bulletin 1926, vol. 80, p. 11.
Pharm. Formulas, vol. 1, pp. 299, 684 & 702.
Bennett Cosmetic Formulary, 1937, pp. 81 & 83.

*Primary Examiner*—Dale R. Ore
*Attorney, Agent, or Firm*—Carver and Company

[57] ABSTRACT

An emulsion consisting essentially of alcohol, pine tar, and mineral oil wherein pine tar and alcohol are mixed before adding the mineral oil so that the composition is essentially an emulsion.

1 Claim, No Drawings

METHOD OF EMULSIFYING MINERAL OIL

BACKGROUND OF THE INVENTION

1. Field of the Invention

This invention relates to emulsions such as which contain alcohol and mineral oil and in particular to a method of mixing.

2. Prior Art

Use of emulsifying agents to obtain homogenous mixtures of otherwise separable liquids in a mixture is well known. U.S. Pat. No. 1,109,119 to Ellis teaches the use of soap solution for emulsifying pine oil and water. Badertscher in U.S. Pat. No. 1,938,752 also teaches the use of soap as an emulsifier to emulsify pine oil and alcohol. Neither of these patents, however, teach a method emulsifying mineral oil and alcohol — oil and alcohol being components of lotions such as sun lotions.

Mineral oil and alcohol usually separate and, unless well mixed by virorous shaking immedately before being applied to a surface, non-uniform application can result. Thus where a sun tan lotion containing mineral oil and alcohol is used an uneven tan is likely to result and, what can be more serious some areas are inadequately protected so as to become burnt — perhaps badly.

SUMMARY OF THE INVENTION

The present invention is based on the discovery that when alcohol and pine tar are thoroughly agitated a liquid is obtained which, when mineral oil is added, further agitation results in a liquid which, essentially, is an emulsion from which the mineral oil does not readily separate out. The emulsion when applied to the skin gives uniform protection materially reducing disadvantages above without vigorous shaking which is required in many known lotions.

Further the emulsion not only gives protection as a sun tan lotion but serves effectively as an insect repellent.

A detailed description following, gives exemplification of method according to the invention which, however, is capable of expression in method and means other than those particularly described and illustrated.

DETAILED DESCRIPTION

Examples

In accordance with the invention two examples of lotions containing mineral oil, alcohol and pine tar are given below, proportions being expressed as parts by weight.

Example 1

Alcohol — 1 part
Pine tar — 1 part
Mineral oil — 3 parts

Example 2

Alcohol — 9 parts
Pine tar — 1.5 parts
Mineral oil — 21 parts

In each of the examples given above isopropyl alcohol and North American pine tar are used. The mineral oil used in both examples is a light petrolatum produced by the Imperial Oil Company of Canada Limited and sold under the trade mark MARKOL.

In both examples the alcohol and pine tar are thoroughly mixed by agitation, the oil then added and the resultant mixture shaken until the oil is essentially emulsified.

No separation of oil and alcohol was observed. Furthermore, both lotions spread evenly when applied and both served, effectively, as insect repellents.

I claim:

1. A method for producing a stable emulsion of light mineral oil and isopropyl alcohol consisting of:
   a. thoroughly mixing one part by weight of North American pine tar with between one and five parts by weight of isopropyl alcohol, and subsequently
   b. adding between two and three parts light mineral oil and violently agitating the mixture of alcohol, pine tar and light mineral oil until a stable emulsion is obtained.

* * * * *